United States Patent [19]
Doll

[11] 3,994,285
[45] Nov. 30, 1976

[54] REVOLVING SYMMETRICAL MAGNET ASSEMBLY AND IMPROVED METHOD OF BLOOD FLOW DETECTION

[75] Inventor: Henry Georges Doll, New York, N.Y.

[73] Assignee: Doll Research, Inc., New York, N.Y.

[22] Filed: Dec. 17, 1974

[21] Appl. No.: 533,528

[52] U.S. Cl. .................. 128/2.05 F; 73/194 EM; 324/34 FL
[51] Int. Cl.[2] .......................................... A61B 5/02
[58] Field of Search ................. 128/2.05 F, 2.06 B, 128/2.05 R; 73/194 EM, 196; 324/34 FL

[56] References Cited
UNITED STATES PATENTS

| | | | |
|---|---|---|---|
| 2,896,451 | 7/1959 | Rinia | 73/194 EM |
| 3,058,458 | 10/1962 | Daneman | 128/2.06 B |
| 3,631,718 | 1/1972 | Sato et al. | 73/194 EM |
| 3,759,247 | 9/1973 | Doll et al. | 128/2.05 F |
| 3,809,070 | 5/1974 | Doll et al. | 128/2.05 F |

FOREIGN PATENTS OR APPLICATIONS

| | | | |
|---|---|---|---|
| 1,914,335 | 12/1970 | Germany | 73/194 EM |

*Primary Examiner*—William E. Kamm
*Attorney, Agent, or Firm*—Kenyon & Kenyon Reilly Carr & Chapin

[57] ABSTRACT

A pair of magnets is adapted to be rotated into several positions around the periphery of a limb for the purpose of producing the magnetic field used in blood flow measurements. Electrodes are arranged in pairs located diametrically opposite each other on the limb. The blood flow measurements are obtained by sequentially monitoring each pair in the array of electrodes located on the skin of the limb so as to obtain blood flow measurements at a plurality of circumferential locations on the limb. Each measurement is stored in a memory, with the heartbeat providing the timing reference. The averaged contributions of each of the several arteries in the limb are picked up by the electrodes to provide a valid total measurement of the overall blood flow in the limb.

5 Claims, 34 Drawing Figures

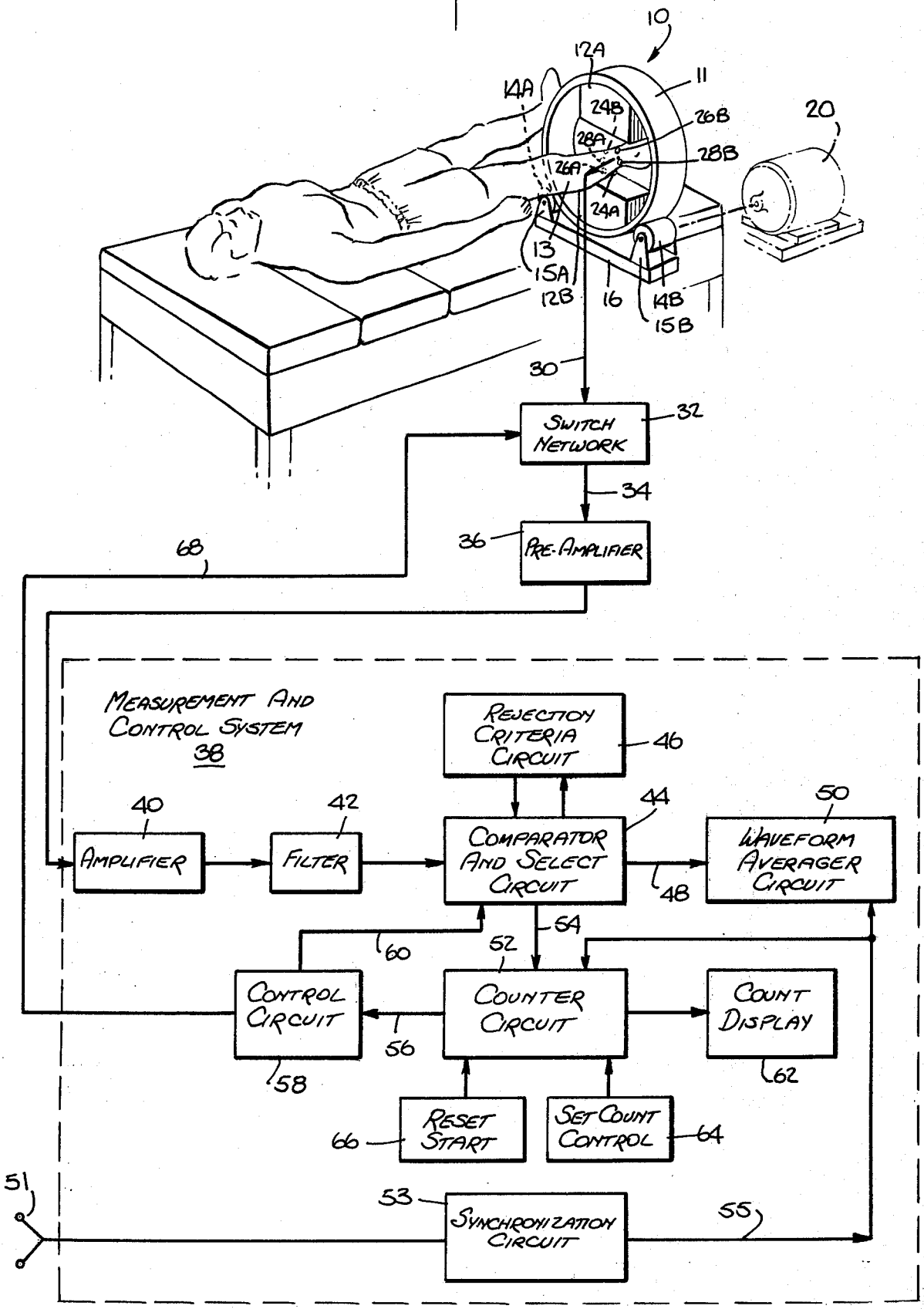

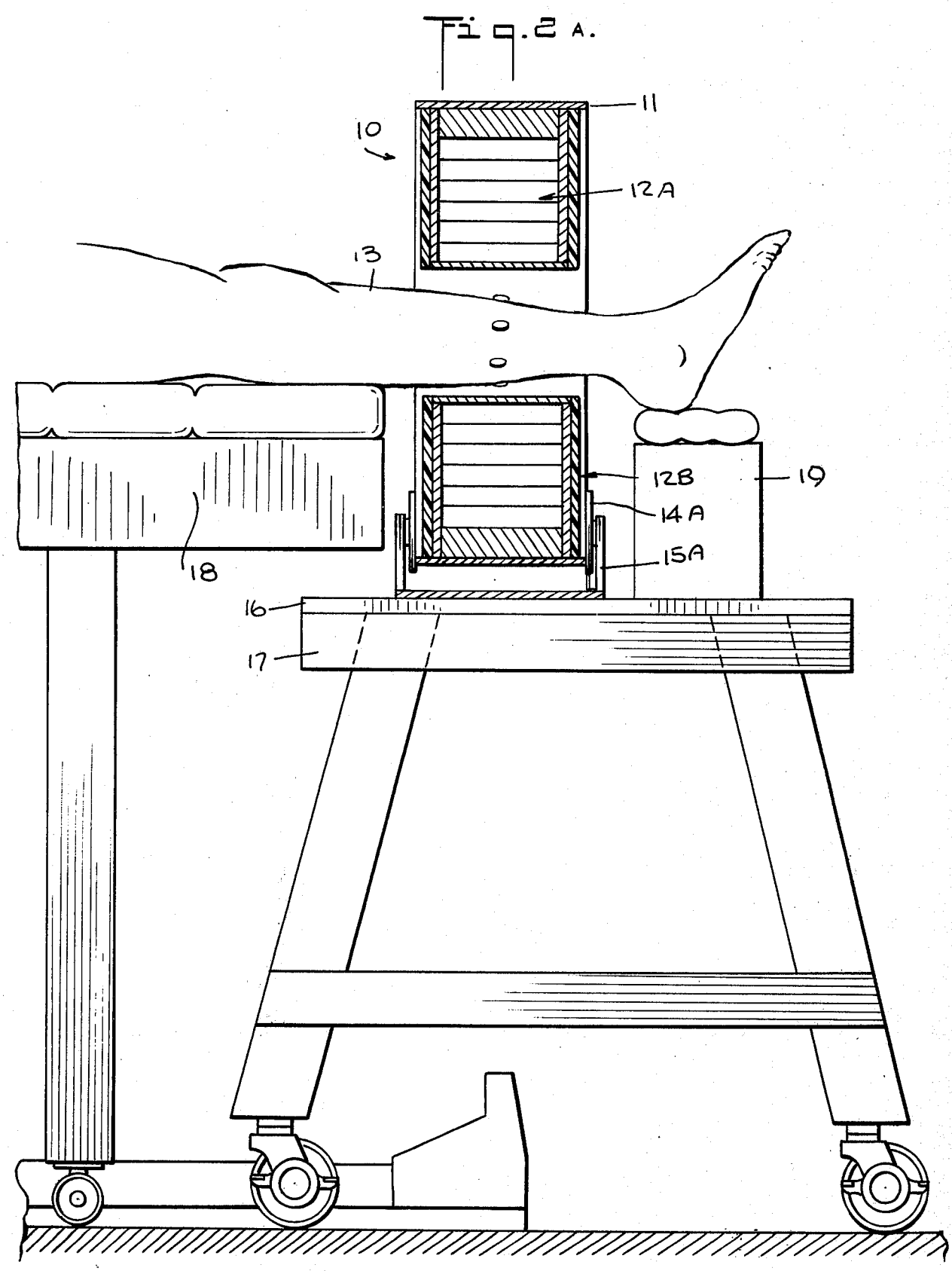

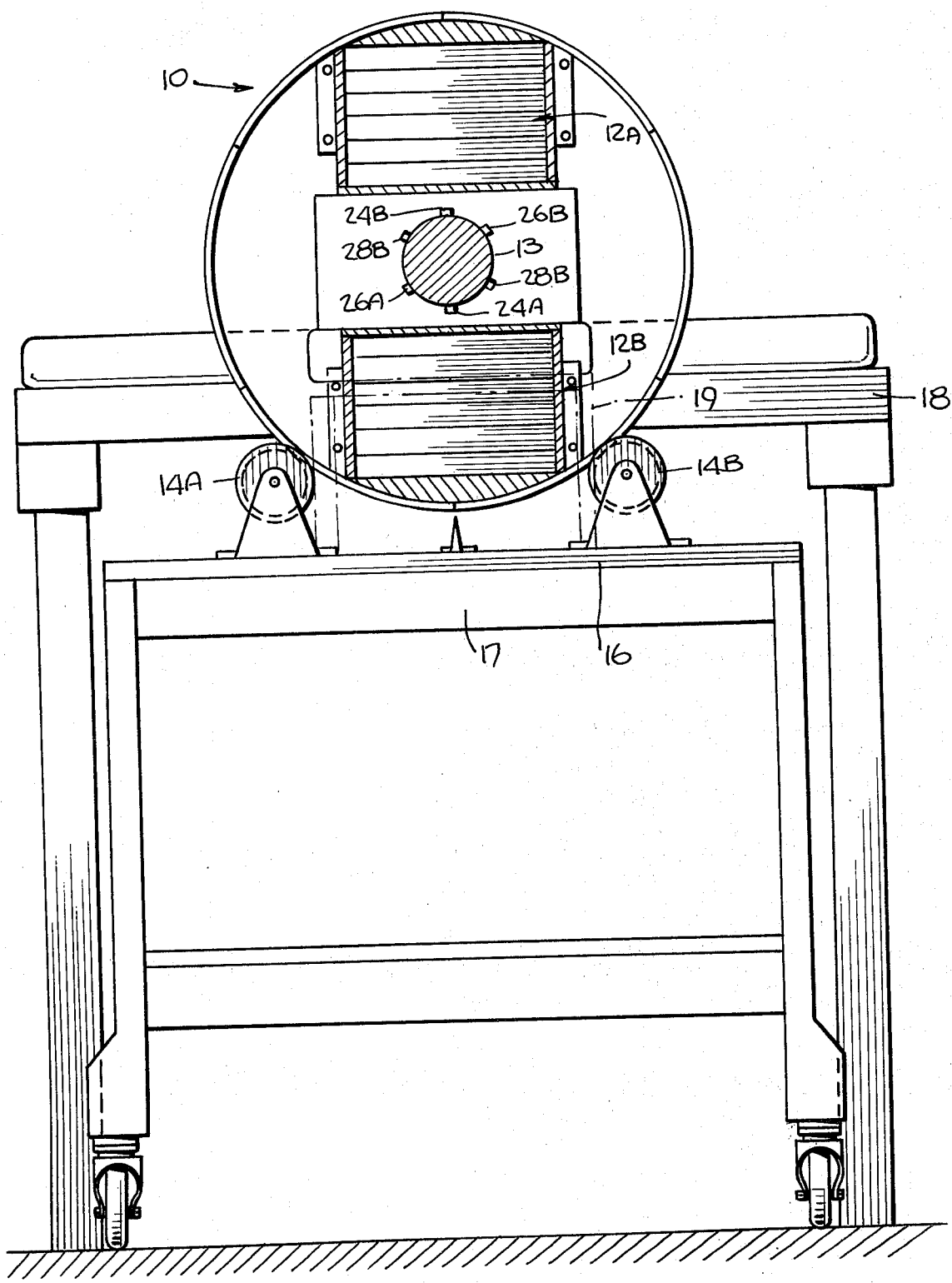

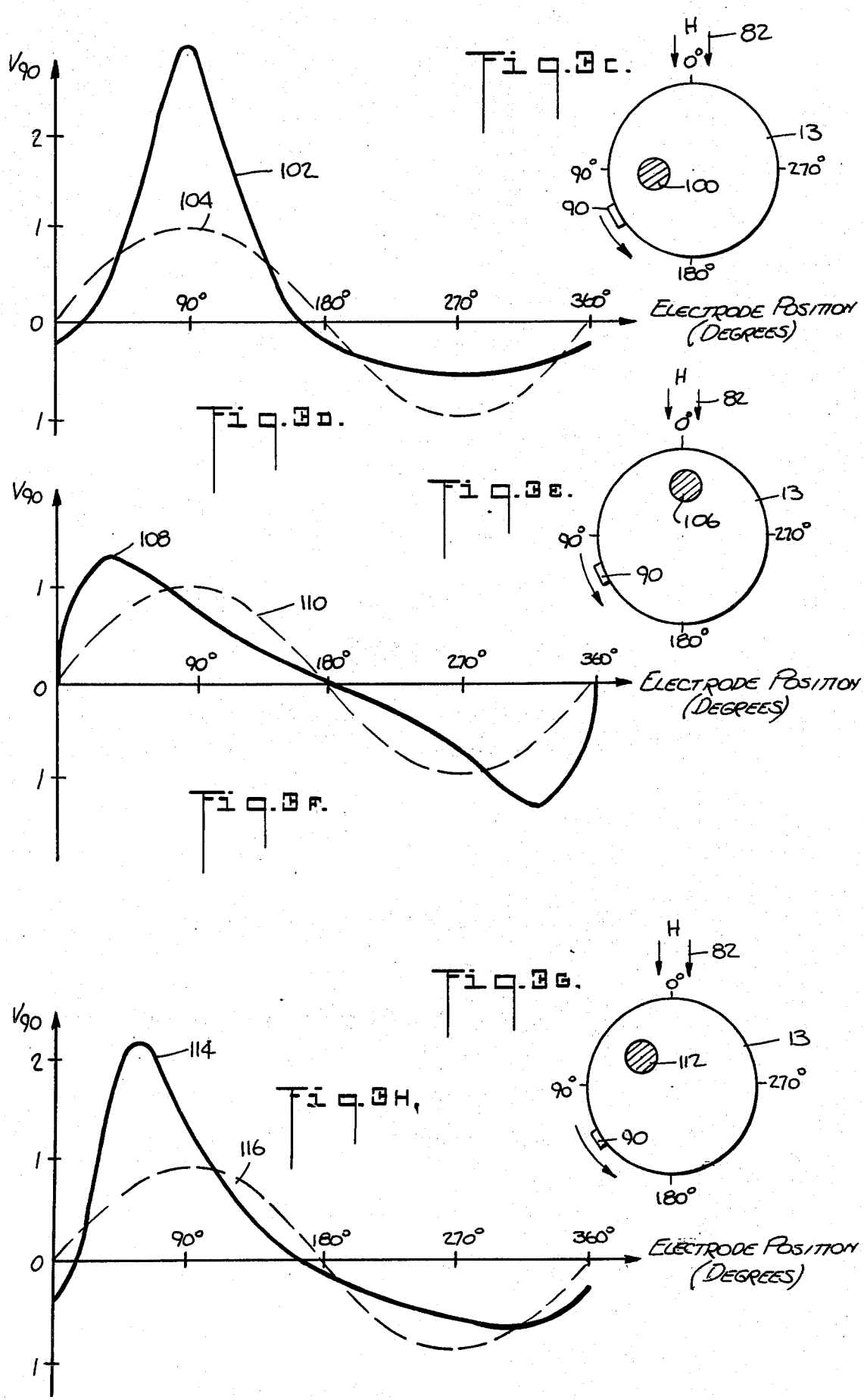

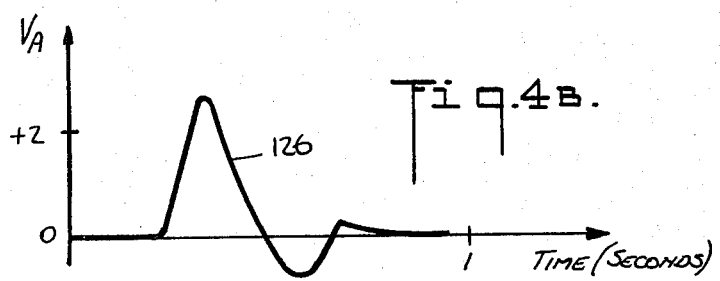
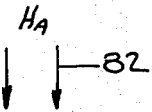
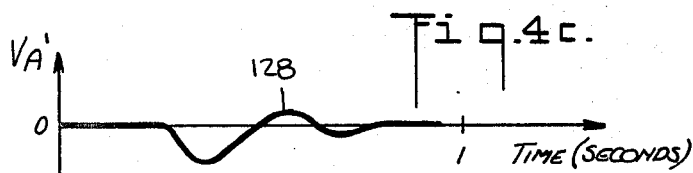
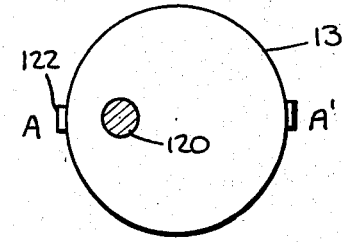
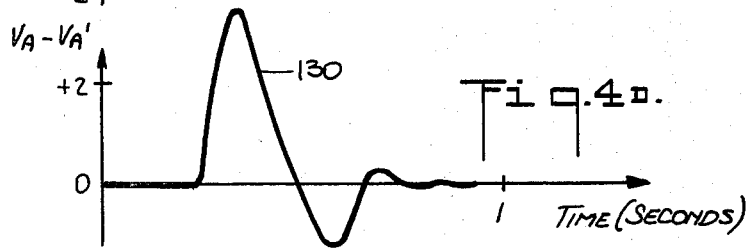
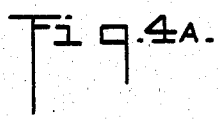
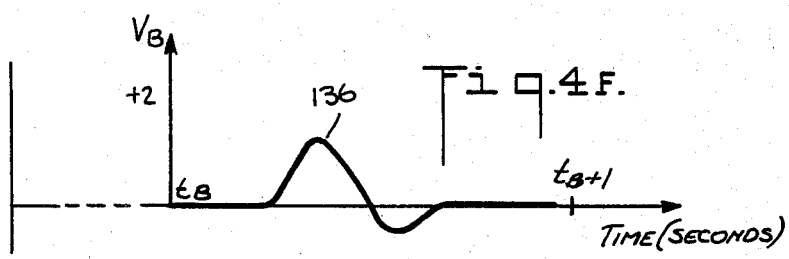
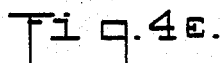
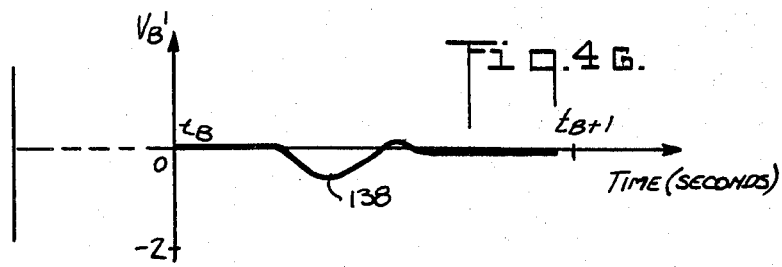
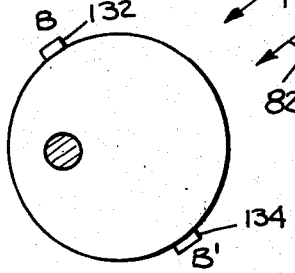
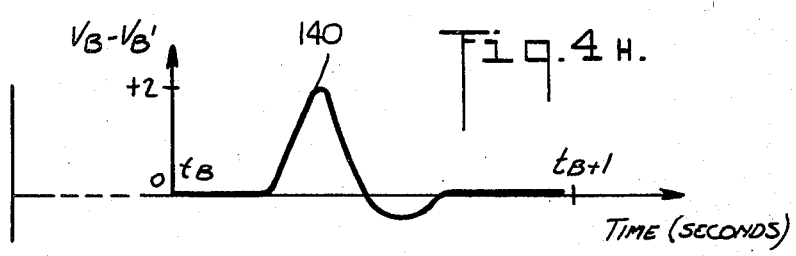

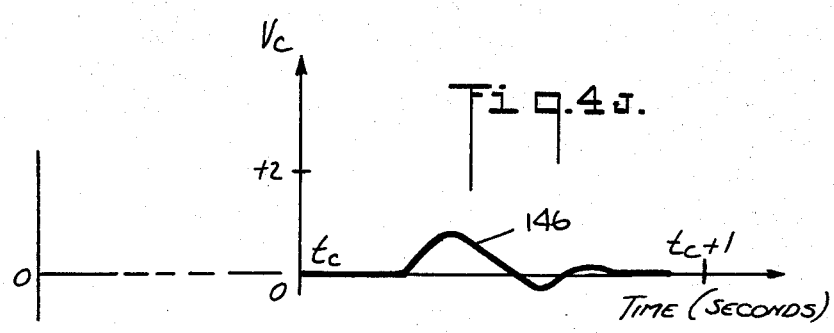
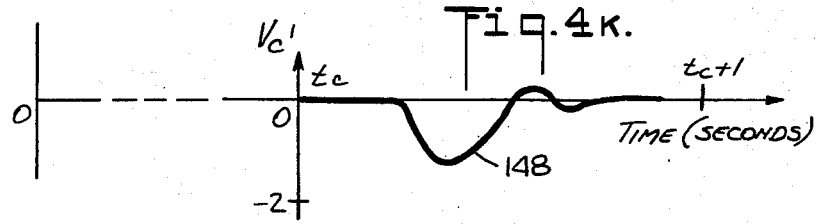
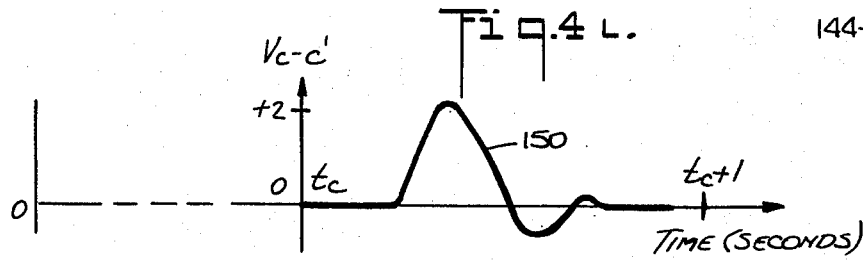
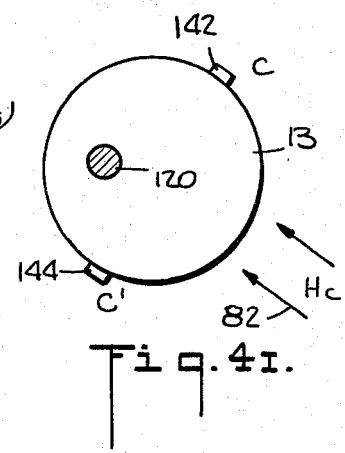
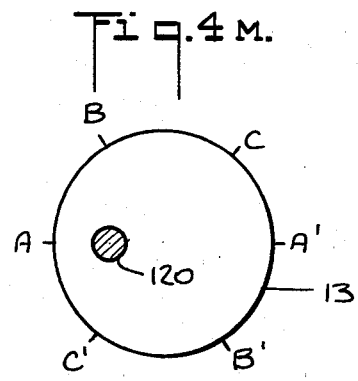
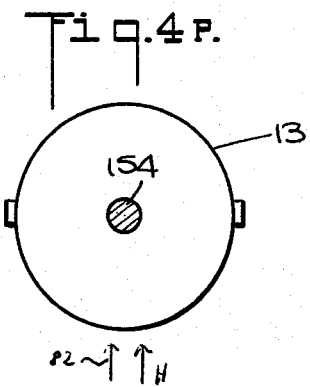
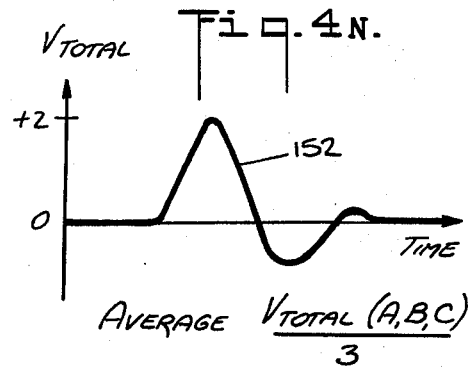
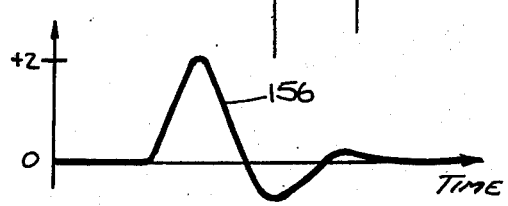

REVOLVING SYMMETRICAL MAGNET ASSEMBLY AND IMPROVED METHOD OF BLOOD FLOW DETECTION

BACKGROUND OF THE DISCLOSURE

The present invention relates to the measurement of blood flow on the limbs of a living being.

Electromagnetic flowmeters are known for measuring blood flow with a pair of electrodes located near the artery under measurement and a magnetic field applied in the region of the artery. A flow related voltage appears between the measuring electrodes which is subsequently amplified and diagnosed by electronic equipment. Such measurements can be made using the apparatus and method described in U.S. Pat. Nos. 3,659,591, 3,759,247 and 3,809,070 issued to the assignee of the present application.

It has been found that some limbs are so poorly supplied with blood that a medical doctor can not detect any substantial pulsation of blood. In such cases, the above blood flow measuring devices might not provide a sufficient blood flow signal at the pair of measuring electrodes.

In a $Hq$ diseased limb, one of the central vessels may be clogged so as to distort the voltage distribution on the limb in a way which is unknown to the clinical investigator. In addition, there is a tendency for the body to replace the nonoperative vessel by newly enlarged collateral vessels. It is practically impossible for the investigator to know where these collateral vessels are located. In the case where such a vessel is closer to the $Hq$ of the limb, at some specific positions, one can possibly obtain a wrong reading from the contribution of this vessel, because the voltage which it contributes is concentrated over a small area of the skin.

Also, in the case of the diseased limb, the total blood flow is very reduced and, consequently, the induced electric signal becomes extremely small. As a result the smallest artifact can create a voltage which could overpower or swamp the blood flow signal.

SUMMARY OF THE INVENTION

Therefore it is an object of the present invention to provide an apparatus and method for measuring blood flow in the limb of a living being. It is another object to provide for measurement of blood flow in the limb which is poorly supplied with blood so that a generally weak signal is picked up by the measuring electrodes. It is a further object to provide for measurement of blood flow in the limb where the location of the blood vessels contributing the largest blood flow signals are unknown.

These and other objects are achieved by the present invention which provides a pair of spaced magnets adapted to be positioned in several diametrically opposed positions around the periphery of a limb. The magnets provide a stable and strong homogeneous magnetic field in the vessels of the limb. The blood flow measurements are obtained by monitoring an array of electrodes positioned on the skin around the limb so as to obtain measurements at a plurality of circumferential locations which can be waveform averaged. The electrodes are arranged in pairs located diametrically opposite each other on the limb. The magnetic field is perpendicular to the limb and can be oriented to be perpendicular to the electrode pair while in use. For a given pair of electrodes located diametrically opposite each other on the limb, a blood flow induced voltage is produced by one or more arteries which, in a healthy person, are located in the central part of the limb.

Through the use of several pairs of such diametrically placed electrodes around the circumference of the limb, measurements of several arteries located in the limb can be made by the angular positioning of the magnets around the limb while successively monitoring respective pairs of electrodes. The averaged contribution of all of the several arteries provides a total measurement of the overall blood flow in the limb, with a fairly good approximation of the value which would have been obtained, if each and every artery could have been measured individually.

It is to be understood that as used herein, the term "monopolar potential" is defined as the voltage at a single electrode, and the term "bipolar potential" is defined as the voltage difference between a pair of electrodes. "Peak value" is defined as the voltage at the time of peak flow. A "waveform" is defined as a time variable representation of the blood flow within its cycle.

BRIEF DESCRIPTION OF THE DRAWINGS

FIG. 1 is a schematic diagram of the system including the rotatable magnet assembly situated near a patient's bed, and the measurement and control system illustrative of the present invention;

FIGS. 2A and 2B show the rotatable magnet assembly shown in FIG. 1;

FIGS. 3C-3H are graphs of the monopolar voltage amplitudes at the time of peak flow of a single electrode at the various positions on the skin of a limb where the artery is located at the various illustrated off-centered positions in the limb;

FIGS. 4A-4L show the pulsatile blood flow waveforms picked up by a pair of diametrically placed electrodes on the limb where the artery is off-center in such limb, such waveforms indicating the time variable voltages at various electrode positions on the limb surface for several different orientations of the magnetic field;

FIGS. 4M and 4N illustrate the summation of the waveforms picked up by the electrodes at various positions on the limb surface around an off-centered artery during the different orientations of the magnetic field as illustrated in FIGS. 4A-4L;

FIGS. 4P and 4Q illustrate as a reference the blood flow waveform picked up by a pair of diametrically positioned electrodes on the skin of a limb having a centrally located artery;

FIGS. 5A-5E are curves of the peak values of the bipolar voltage taken at one or more pairs of electrodes for the situation where an off-centered artery is located at different orientations around the center of the limb and the skin.

DESCRIPTION OF THE PREFERRED EMBODIMENTS

Figure 3A:
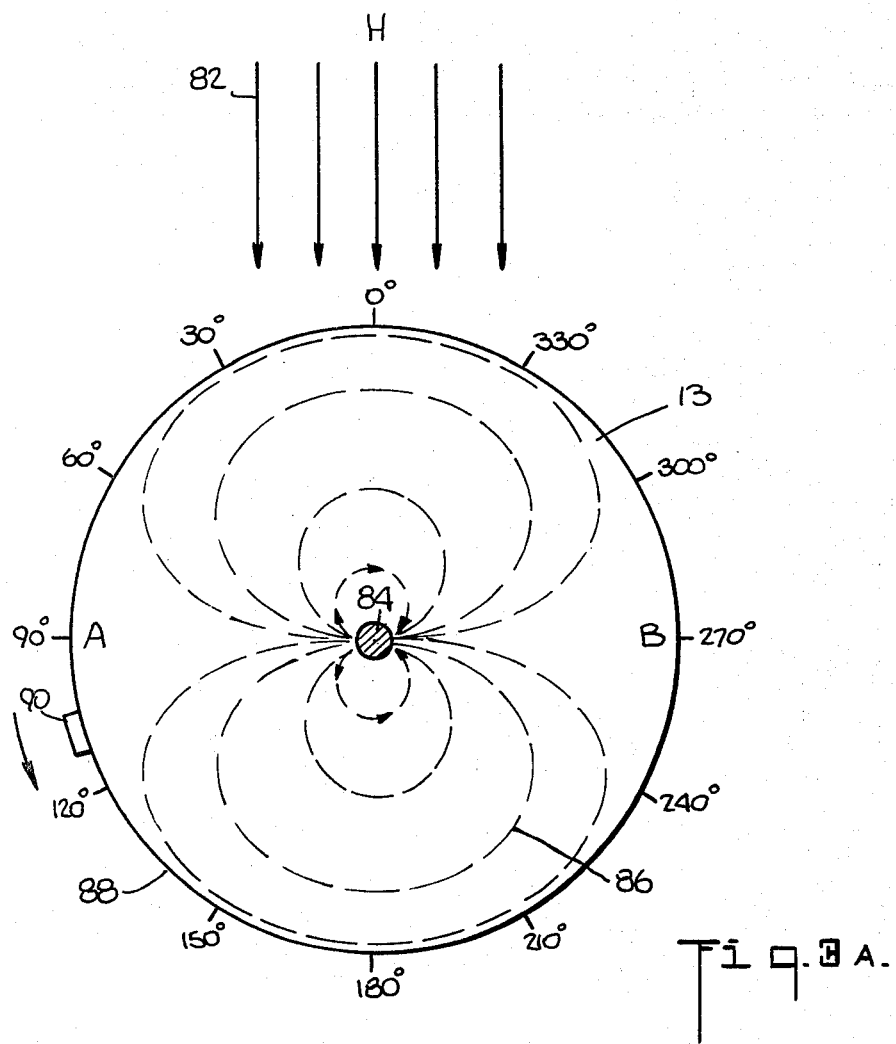
FIG. 3A shows a hypothetical boneless limb in a magnetic field with the current lines generated in the flesh due to the blood flow through a centrally located artery in the limb.

Referring to FIGS. 1, 2A and 2B, there is shown a schematic of the device according to the present invention. The device generally provides for the measurement of blood flow of the arteries in the limbs and may employ the general magnetic field producing elements, electrode devices and waveform averaging techniques disclosed in the above noted patents. In this configuration, a rotatable magnet assembly 10 includes a pair of permanent magnets 12A and 12B mounted on a metal ring 11 which is physically revolved around the limb 13. The metal ring 11 is rotatably mounted on ballbearing rollers 14A and 14B which in turn are supported by rigid supports 15A and 15B on a base 16. The base 16 of the assembly 10 lies on top of a table 17 that can be rolled into position adjacent a patient's bed 18. A heel support 19 is also provided on the table 17. The magnets 12A and 12B are fixedly secured to the ring 11. Ring 11 is a circular piece of soft iron constituting a pole piece for magnets 12A and 12B providing a closed path for the magnetic field. As shown, the permanent magnets 12A and 12B are placed on the opposite sides of the limb 13 in a Helmholz configuration which provides a strong, constant and homogeneous magnetic field. Each of the magnets 12A and 12B may, for example, comprise six magnetic blocks having dimensions of about 4 inches by 7 inches by 1 inch which form an overall magnetic block having dimensions of 4 inches by 7 inches by 6 inches. The magnets 12A and 12B may be comprised of conventional permanent magnetic material, such as barium ferrite, producing a magnetic field having a strength of about 900 gauss. The operation and function of permanent magnets in blood flow meter measurements is further disclosed in U.S. Pat. Nos. 3,759,247 and 3,809,070. The magnets 12A and 12B may be rotated on the ring 11 and rollers 14A and 14B by the medical technician or alternatively, by means of a motor device 20. The ring 11 is rotated by the technician or by driving the roller 14B by the motor device 20 to index the magnets 12A and 12B concentrically around the limb 13 of a patient who may be in a lying position.

A plurality of pairs of electrodes shown as 24A and 24B, 26A and 26B and 28A and 28B are placed generally circumferentially around the limb 13 to permit pick-up of the blood flow induced electric signals caused by the blood vessels such as A1, A2 and A3 shown. It is noted that for purposes of explaining the invention, three pairs of electrodes are shown although the number of electrodes can vary in accordance with the requirements of each situation. For reasons which will be explained in a portion of this specification, each pair of electrodes are shown diametrically placed on the limb 13 although the electrode pairs can also be spaced apart on the skin generally near the same plane.

Each of the electrodes 24A and 24B, 26A and 26B and 28A and 28B are connected by individual wires indicated by numeral 30 which connects with a switch network 32. Switch network 32 may comprise a mechanical, hand-operated switch or a conventional electronic gate switching network for connecting a single pair of electrodes via their respective wires 30 to the output lines 34 of the switch network 32. The electrical pick-up from each switched-in electrode is a monopolar voltage, variable during the heart cycle. The other electrode of the pair provides also a different monopolar voltage, usually of the opposite polarity at any given moment. Both voltages are amplified by a differential pre-amplifier 36 and the combined bipolar signal thereafter processed in a measurement and control system 38 such as the blood flow measuring system disclosed in the above-mentioned patents.

More specifically, the measuring system 38 includes an amplifier 40 for amplifying the signals from the pre-amplifier 36. The output of amplifier 40 is connected to a filter circuit 42 which reduces unwanted high and low frequency noise, including 60 $H_z$. The filtered signals are then passed on to a temporary single cycle memory and signal selector 44, where they are examined with respect to the predetermined data in a rejection criteria circuit 46, the circuits 44 and 46 being disclosed in detail in U.S. Pat. No. 3,809,070. Each accepted waveform is sent via line 48 to a waveform averager or memorizing system 50, similar to the memory system disclosed in U.S. Pat. No. 3,809,070. This memory has the dual function of waveform averaging at each measurement and storing, additively, the results from a plurality of electrode pairs.

Auxiliary electrodes 51 are placed on the body in a position which is close to the heart to provide an electrocardiogram for use in a synchronization circuit 53 which provides trigger pulses on line 55 for the waveform averager 50. The synchronization circuit also provides a signal to the counter 52 for synchronizing the same. As described in the above-mentioned patents, the synchronizing circuit 53 and the electrodes 51 enable the heart to be used as a synchronizing signal and as a clock for measurement and control system 38. At the same time, a counter circuit 52 is advanced by one count by means of a signal on line 54 to such counter 52 at each instance when a waveform cycle is passed from the circuit 44 in the waveform averager 50. At the completion of the averaging of N acceptable waveforms, the counter 52 provides a pulse via line 56 to a control circuit 58. The control circuit 58 provides a signal on line 60 to the select circuit 44 for inhibiting the collection of additional signals which are sent through the select circuit 44 to the averager 50. The counter circuit 52 is also connected to a count-display device 62 for providing a visual indication of the number of waveforms that have been collected in the waveform averager 50 during a given sequence. A set count control 64 is provided for manually setting the number of waveform counts to be counted by the counter 52 and indicated on the count-display 62 after which the counter can be reset. A reset start control 66 is connected to the counter 52 for manually permitting the counter to operate after it has reached its pre-set count.

After a pre-set number of blood flow waveforms determined by the set count control 64 have been stored in the waveform averager 50, the counter 52 provides an inhibiting signal on line 56 which in turn is passed on to the select circuit 60 for inhibiting the further entry of waveforms into the averager 50. At this time, the control circuit 58 provides a signal on line 68 to the switch network 32 for advancing the switch to the next pair of electrodes on the limb. For example, if the previous pair of electrodes 24A and 24B were connected to the pre-amplifier 26 by the switch network 32, then the control circuit 58 would advance the switch network 32 to connect electrodes 26A and 26B to the lines 24 leading to the preamplifier 26. It is noted that the switch network 32 might also comprise a manual switch for making the same connection. In addition to the switching in of electrodes 26A and 26B into the system, the magnets 12A and 12B are also indexed into position on a line perpendicular to a line between such electrodes so that the optimum field is produced in the region of the limb being detected by the electrodes 26A and 26B. At this time, the reset start control 66 is operated to initiate the start of the counter 52. Simultaneous with the start of the counter 52 there is provided a signal on line 56 which is passed by the control circuit 58 to the select circuit 44 via line 60 for permitting another series of waveforms to be accumulated in the averager 50. It is to be noted that the control circuit 58 may comprise a simple gate which produces a binary output on line 60 which inhibits or enables the select circuit 44 to pass signals to the averager 50. The gate in control circuit 58 may produce a first level output when the counter 52 arrives at its pre-set number, and will produce second level output when the counter 52 is reset to zero by the reset start control 66.

In this fashion, the blood flow measurement operation is carried out by positioning the magnets 12A and 12B in proper positions with respect to the pairs of electrodes that are switched in to provide the pick-up signals that are entered at any given time through the switch 32 into the measurement and control system 38. As a given pair of electrodes is electrically connected into the system, the permanent magnets 12A and 12B are positioned to create a magnetic field perpendicular to the switched-in pair of electrodes.

It is to be pointed out that the system disclosed in FIG. 1 can be operated in a manner whereby the permanent magnets 12A and 12B are rotated 180° after a first series of a predetermined number of blood flow waveforms are picked up and accumulated in the waveform averager 50. Such rotation of the permanent magnets reverses the polarity of the magnetic field and consequently the polarity of the blood flow induced signal picked up by the electrodes. As described in each of the previously mentioned U.S. Pat. Nos. 3,659,591, 3,759,247 and 3,809,070, the reversal of the magnetic field together with the reversal of the polarity of the signal entering the averager 50 acts to cancel out any contribution of the cardiogram to the signals picked up by the blood flow electrodes. For measurements on the calf, this alternative procedure of reversing the magnetic field for a second set of blood flow waveforms to compensate the electrocardiogram components in the signal is not always needed since the electrocardiogram component on the calf is essentially negligible. However, the use of the field reversal procedure is advantageous in that the sensitivity of the measurements is doubled by accumulating an additional set of blood flow waveforms in the averager 50.

It is known that the placing of the electrodes on the skin as well as the amount by which the line between the electrodes is offset from the blood vessel can greatly alter the sensitivity and output of the electrodes. In situations where the blood circulation is not in the central area of the limb, as would be the case of the blood clot of the major vessels, then the circulation in the limb will be of a collateral nature and one will be unable to readily ascertain where the blood is flowing in the limb. It has been found that when an artery is more or less centrally located in a limb and when a magnetic field is applied perpendicular to the direction of the vessel, a flow related voltage is produced at a pair of electrodes located diametrically opposite each other on the limb and in a plane perpendicular to the magnetic field. This diametric placement of the electrodes has been found to produce sufficiently high output signals with relatively less sensitivity of the measurements to deviations of the blood vessel from the diametric position, and to the influence of the bones.

Thus, in situations of blood clots, where the major location of the collateral blood circulation in the limb is not known, the diametric placement of the electrodes enables a sufficient detection of the signals produced by the blood vessels in the area between the electrodes. Also, in accordance with the invention, diametric placement of the electrodes has been found to produce good measurement results for not only the central artery but also the grouping of several arteries in the limb. The signal contribution of each of the several arteries provides a total average blood flow signal at the electrodes which is subsequently waveform averaged in the measurement and control system 38, shown and described with reference to FIG. 1.

Figure 3B:
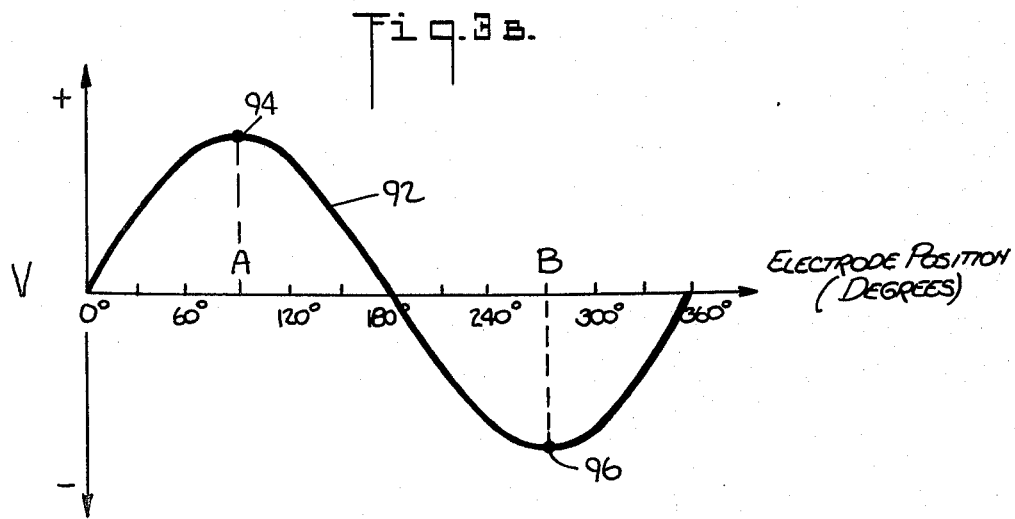
FIG. 3B shows the peak values of the monopolar voltage at the time of peak flow for a single electrode located at each circumferential position on the skin of the limb shown in FIG. 3A.

FIG. 3A shows a limb 13 in a magnetic field H, indicated by arrows 82, with the current lines 86 generated in the flesh due to the blood flow through a centrally located artery 84 in the limb 13. FIG. 3B shows the peak values of the monopolar voltage 92 observed when changing the circumferential placement of a mobile electrode 90 on the skin 88 of the living being with respect to location of the blood vessel 84 under study, when the vessel is known to be at the center. The diametric locations A and B appear to be optimal as indicated by the points 94 and 96 on the curve 92 at the 90 degree and 270 degree electrode positions.

FIGS. 3C–3H are further limb diagrams and associated graphs of the peak values of the monopolar voltage amplitudes of the single electrode 90 at the various positions on the skin of a limb where the artery is located at the various illustrated off-centered positions in the limb. Specifically, FIG. 3C shows the condition where an artery 100 is located off-center as illustrated, and FIG. 3D is a graph having a curve 102 of the peak values of the monopolar voltage observed when changing the circumferential placement of the electrode 90. Also, the dotted curve 104 represents the peak values for the reference condition where the artery is centrally located. FIG. 3E shows the condition where an artery 106 is located off-center as illustrated, and FIG. 3F is a graph having a curve 108 of the peak values of the monopolar voltage observed for the different placements of electrode 90. In FIG. 3F, the reference centrally located artery is indicated by the dotted curve 110. FIG. 3G similarly shows the condition where an artery 112 is located off-center as illustrated, and FIG. 3H is a graph having a curve 114 of the peak values of the monopolar voltage observed for different placements of electrode 90. In FIG. 3H, the reference voltage for the centrally located artery is indicated by the dotted curve 116.

FIGS. 4A through 4Q illustrate the measurement with the method of using three pairs of electrodes by showing the history of individual waveforms, as stored in the memory, and the result of the summation of the three individual measurements. The zero time is indexed by the R wave of the synchronizing electrocardiogram. More specifically, FIGS. 4A–4L show the pulsatile blood flow waveforms picked up by a pair of diametrically placed electrodes on the limb where the artery is off-center in such limb, such waveforms indicating the time variable voltages at various electrode positions on the limb surface for three different orientations of the magnetic field. In such figures, there are employed different sequential orientations of the magnetic field while a respective pair of electrodes is switched in, which is perpendicular to the magnetic field. In FIG. 4A, diametrically positioned electrodes 122 and 124 are located at points A and A' on the limb 13 having an artery 120 located at the position shown. The electrodes are perpendicular to the field $H_A$ indicated by the arrows 82. FIG. 4B is a graph of the monopolar waveform $V_A$ of the electrode at the position A and is depicted by the curve 126. FIG. 4C is a graph of the monopolar waveform $V_{A'}$ at the electrode 124 in position A' and is depicted by the curve 128. FIG. 4D shows the waveform of the bipolar waveform $V_{A-A'}$ between electrodes 122 and 124, and is depicted by the curve 130.

FIG. 4E shows a pair of electrodes 132 and 134 diametrically positioned on the limb 13 perpendicular to the field $H_B$ indicated by arrows 82. Here, the artery 120 is located as shown in FIG. 4E, and the electrodes 132 and 134 are located at the positions B and B'. FIG. 4F is a curve of the monopolar waveform $V_B$ at the electrode 132 and is indicated by the curve 136. FIG. 4G shows the monopolar waveform $V_{B'}$ at the electrode 134 and is indicated by the curve 138. FIG. 4H is a waveform of the bipolar voltage $V_{B-B'}$ between the electrodes 132 and 134 and is indicated by the curve 140.

FIG. 4I shows a pair of electrodes 142 and 144 diametrically positioned at the points C and C' on the limb 13, with such electrodes perpendicular to the magnetic field $H_C$ indicated by arrows 82. Here, the artery 120 is located at the position shown. FIG. 4J shows the monopolar waveform $V_C$ at the electrode 142 and is indicated by the curve 146. FIG. 4K shows the monopolar waveform $V_{C'}$ at the electrode 144 and is indicated by the curve 148. FIG. 4L is the bipolar waveform $V_{C'-C'}$ between the electrodes 142 and 144 and is indicated by curve 150.

FIG. 4M depicts the limb 13 and the same artery 120 located halfway between the center of the limb and the skin and the positions A, A', B, B', C and C' on the skin which provide the above mentioned waveforms 130, 140 and 150. FIG. 4N illustrates the summation of the waveforms 130, 140 and 150 as represented by the curve 152. Actually this summation of the waveforms is carried out automatically in a computer memory, and thereafter is divided by three to obtain an average representation of the blood flow of the off-centered artery 120. FIG. 4P illustrates as a reference a centrally located artery 154 in the limb 13 with a pair of diametrically positioned electrodes. FIG. 4Q is the pulsatile waveform variable in time, as collected by the electrodes measuring the artery 154 and is represented by the curve 156. Curve 156 is used as a reference waveform for purposes of comparison. It can be seen that the waveform 152 is a close approximation, within about four per cent of the reference waveform 156.

It has been found that when a single pair of electrodes is placed diametrically perpendicular to a magnetic field and on the skin of a limb, the resulting amplitude of the measured flow waveform represented by its peak value varies in dependence on the location of the artery with respect to the pair of electrodes. This is generally shown by the FIGS. 5A and 5B where an artery 170 is located about midway between the center 172 of the limb 13 and the skin 174. If it could be assumed that the arteries 170 were located at various midway positions on the circle 176 and a pair of electrodes 178A and 178B are fixed as shown, then a curve 180 is produced depicting the peak bipolar voltage between said electrodes for the various locations of the artery 170. As shown in FIG. 5B, the maximum output at the electrodes occurs when the artery 170 is located at the 90 degree and 270 degree positions on the circle 176 while the minimum voltage output occurs at the 0 degree and 180 degree positions.

In reality, the unknown artery 170 does not move, but the combination magnetic field with the associated perpendicular electrode pair moves relatively. Therefore the explanation of FIG. 5B depicts also the case where pairs of electrodes are placed at various locations on the skin. A dotted line 182 drawn horizontally in the graph of FIG. 5B indicates the average values of the peak voltages produced by the artery 170 as collected at the different positions. It can be seen that, as the position of the artery is unknown, then a single pair of electrodes can provide a voltage output which deviates by as much as minus 20 per cent to plus 70 per cent of the reference voltage value as in FIG. 4Q.

Figure 5A:
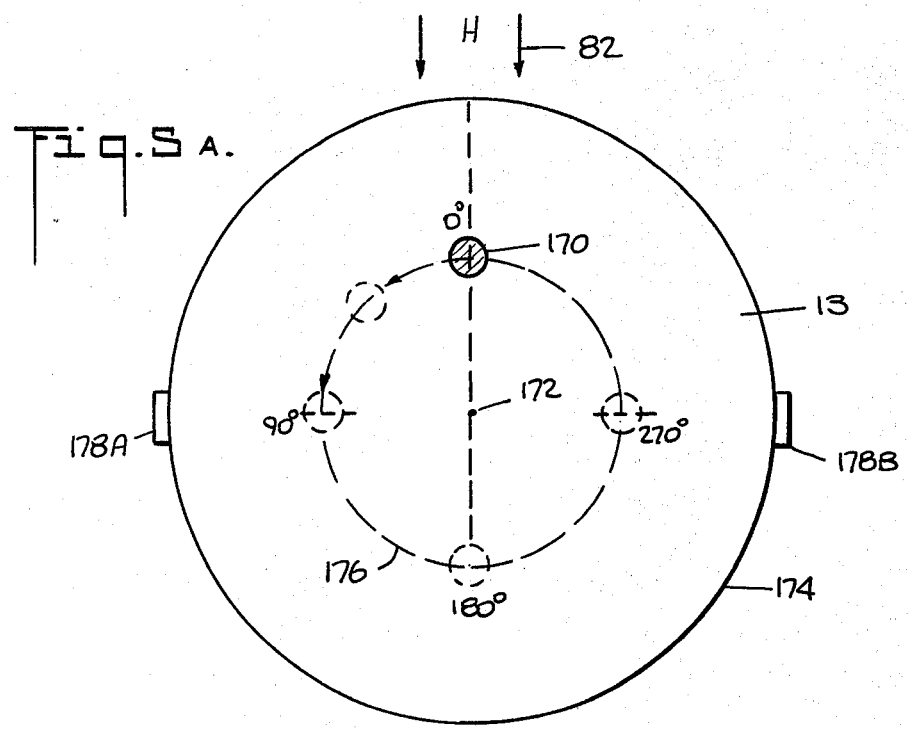
Figure 5B:
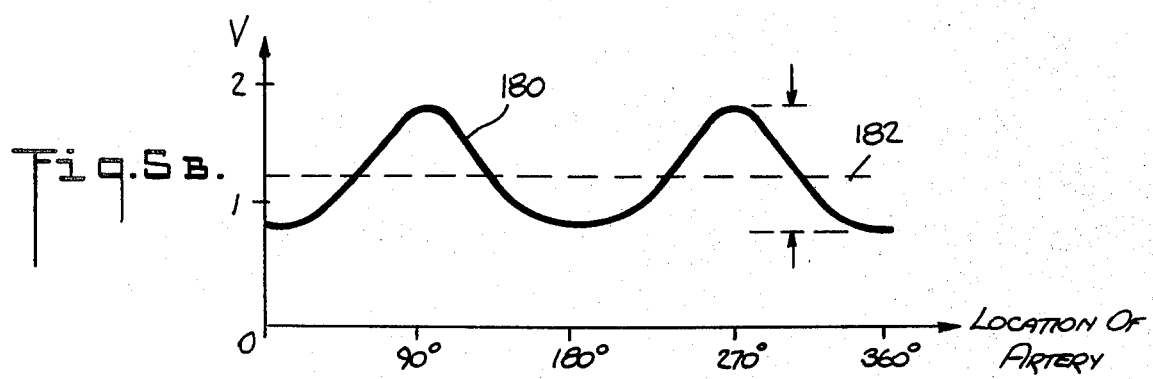
Figure 5C:
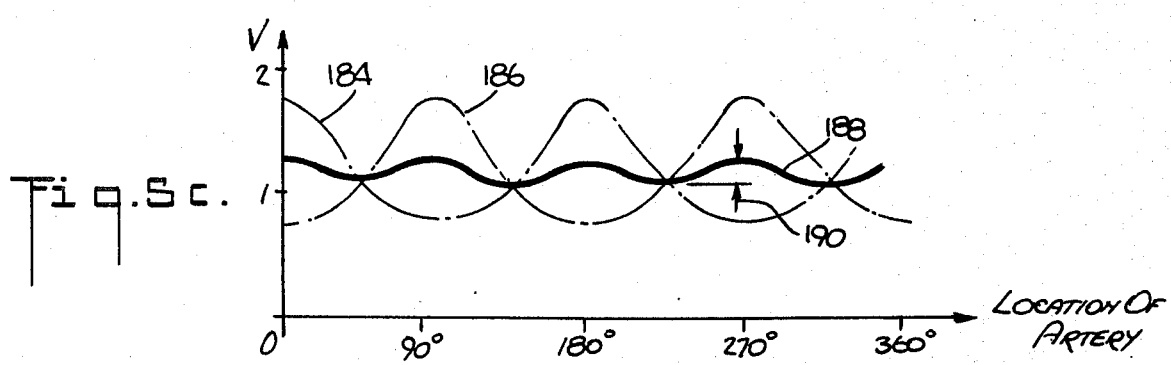

Referring to FIG. 5C, there is shown the relative voltages produced by two pairs of electrodes situated on the skin of the limb and which are offset 90 degrees from each other. Specifically, the curve 184 is produced at a first pair of electrodes, such as the electrodes 178A and 178B shown in FIG. 5A, while a curve 186 is produced at a second pair of electrodes, not shown, situated 90 degrees apart from the first pair of electrodes. A curve 188 shows the averaged values of the two curves 184 and 186. It can be seen by the arrows 190 that the maximum deviation between the maximum and minimum voltage values for the averaged curve 188 for the two pairs of electrodes is about 18 per cent, which is much smaller than the deviation of about 90 per cent in the values of curve 180 shown in FIG. 5B.

Figure 5D:
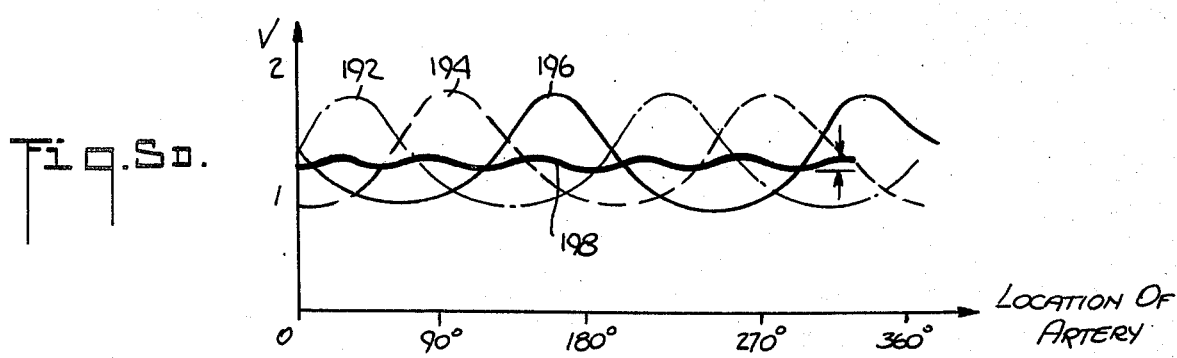

Similarly, as shown in FIG. 5D where three diametrically opposed electrodes are situated 60 degrees apart on the limb, the off-centered artery 170 shown in FIG. 5A provides the voltage waveforms 192, 194 and 196 for the three respective pairs of electrodes. The averaged waveform of the three curves 192, 194 and 196 is shown by the numeral 198 and indicates a maximum voltage deviation of about 2 per cent in the average taken by the three pairs of electrodes. From the above FIGS. 5B, 5C and 5D, it has been graphically illustrated how the wide variation in the electrode output at a single pair of electrodes is substantially reduced by employing several pairs of electrodes for measurement of an off-centered artery while the deviation in measurements for a single pair of electrodes could be as much as about 90 per cent, the deviation is reduced to about 18 per cent when employing two pairs of electrodes, further reduced to about 2 per cent when employing three pairs of electrodes spaced around the circumference of the limb.

Figure 6C:
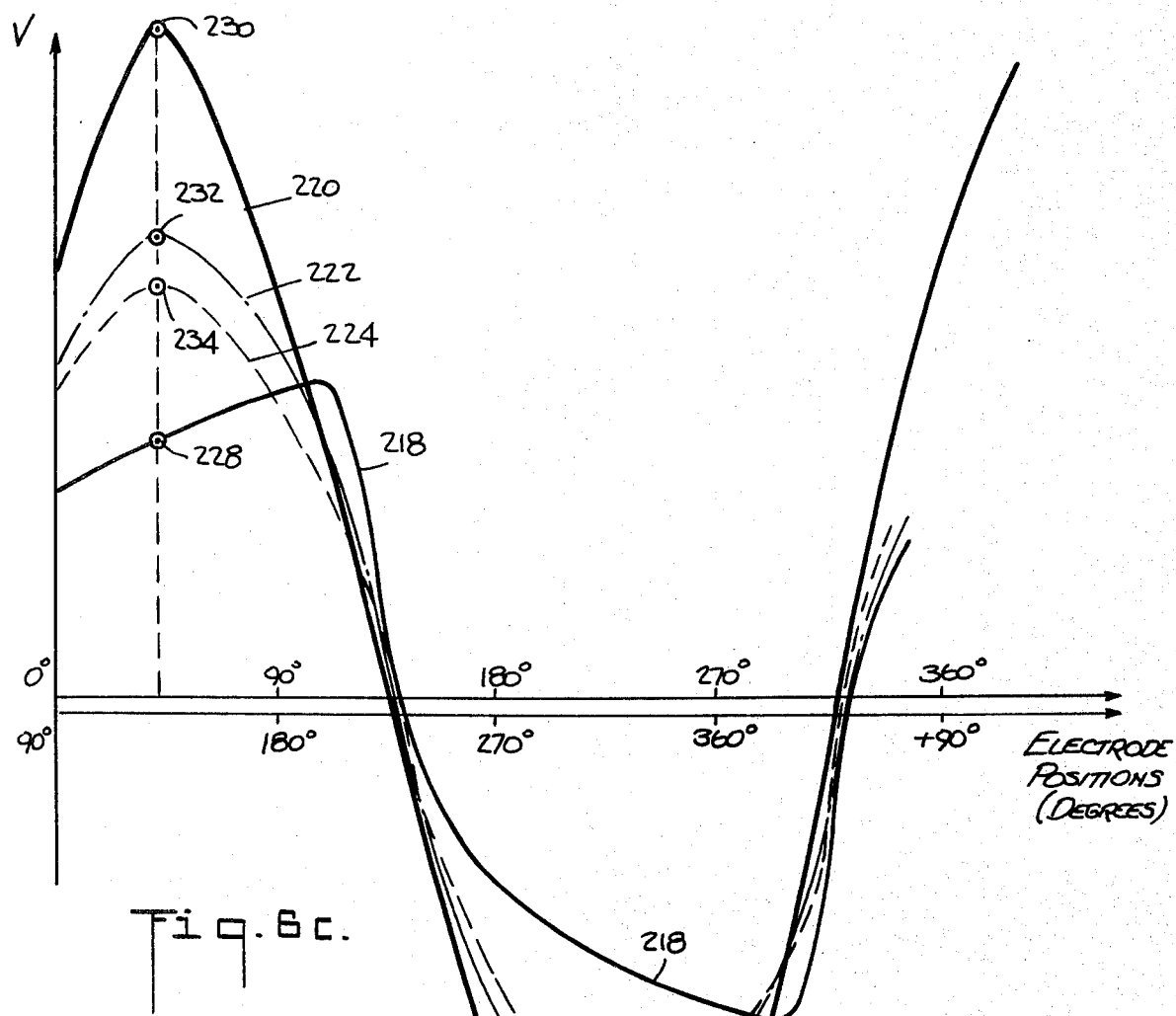
FIGS. 6A and 6B show the limb section and FIG. 6C shows the voltage curves of measurements on a simulated limb, where the bones influence the voltages captured by the electrodes.
Figure 6A:
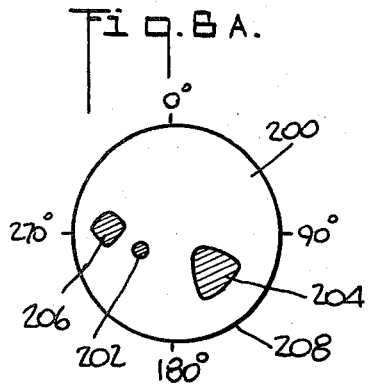
Figure 6B:
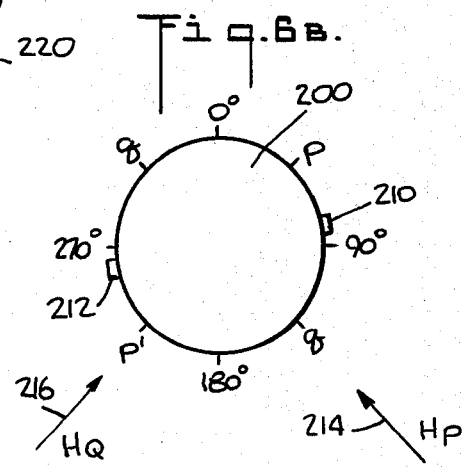

FIG. 6A shows a simulation of a leg 200 at the calf level, such leg 200 having an off-centered artery 202 and bones 204 and 206 representing the tibia and fibula bones, respectively. FIG. 6B shows the skin 208 of the leg 200 with electrodes 210 and 212 diametrically opposed and which scan the skin to record the peak bipolar voltage values created by the blood flow in the artery 202 under the influence of a magnetic field. In FIG. 6B, this magnetic field is first applied in one direction $H_p$ indicated by the arrow 214 after which such magnetic field is rotated into the direction Hg indicated by arrow 216.

Referring to FIG. 6C, there are shown the peak bipolar voltages captured by electrodes 210 and 212 when they are rotated into different circumferential positions on the leg 200. Curve 218 is the peak bipolar voltage occurring under the influence of the magnetic field H$\delta$ shown by arrow 216 in the FIG. 6B at the various circumferential positions of electrodes 210 and 212. The abscissa of the graph represents a linear scale of angles. Magnetic field q is directed at about 45 degrees and the magnetic field Hp, which is directed at about 135 degrees, creates a set of voltages represented by a curve which, in FIG. 6C, has been shifted to the curve 220. Curve 220 is a peak bipolar voltage occurring under the influence of the magnetic field Hp shown by arrow 214. The location of the curve 220 has been shifted on the angular abscissa of the graph of FIG. 6C and 90 degrees in order to place it visually in coincidence with corresponding points of the curve 218 for explanatory purposes. This angular shift of the graphical representation of the voltages is similar to the time positioning in a computer, as is well known in the art. It is noted that the shape of the curves 218 and 220 demonstrate the influence of both the off-centering of the artery 202 as well as the presence of the bones 206 and 204. Curve 222 is the median curve obtained by summing the curves 218 and 220 and dividing this sum by two. For comparative reasons, a curve 224 is shown which represents the theoretical case of a centered artery with the same blood flow, and without the bone perturbation. This reference curve 224 corresponds with the curve 92 of FIG. 3B.

It can be seen that curve 222 is a fairly close approximation of the reference curve 224. In practice, instead of moving the electrodes around the limb, preferred positions are chosen which are perpendicular to the magnetic field. These preferred positions are shown as P and $P^1$ and q and $q^1$, associated with the field directions Hp and Hq, respectively. With the electrodes placed at these preferred positions, the measurement made according to the method described in this invention yields a deviation of about 14 per cent more than the value 234 of the reference curve 224 at the corresponding positions. Successive readings 228 and 230 made individually as on curves 218 and 220 would have yielded individual deviations of plus 43 per cent and minus 33 per cent as compared with the value 234 of the reference curve 224.

Thus, it has been shown how the method of averaging successively in time, with the means of a rotating field and a corresponding plurality of pairs of electrodes allows one to obtain a sufficiently valid measurement 232 in waveform amplitude, of the total blood flow through the limb, even when both bone-obstacles and variation of location exists.

Although the above description is directed to the preferred embodiments of the invention, it is noted that other variations and modifications will be apparent to those skilled in the art, and, therefore, may be made without departing from the spirit and scope of the present disclosure.

What is claimed is:

1. An instrument for measuring the pulsatile blood flow in a limb of a living being, comprising:
    a plurality of electrode pairs adapted to be positioned in diametrically opposed relation at spaced locations on the skin around the limb;
    means for producing a stable and homogeneous magnetic field perpendicular to the limb, the magnetic field having an intensity large enough to produce measurable signals in said electrodes as a result of pulsatile blood flow through at least one arterial vessel in said limb;
    waveform memory means for storing the waveform signals picked up by said electrodes;
    switching means connected between said electrodes and said waveform memory means for selectively switching-in only one of said pairs of electrodes for a first cycle of waveform measurements, and for thereafter successively switching-in the others of said pairs of electrodes, one at a time, for one or more further cycles of measurements;
    means for indexing said magnetic field to be oriented in a direction perpendicular to the line between each selected switched-in pair of electrodes during the corresponding cycle of measurements for each switch-in pair; and
    synchronizing means for providing a time reference signal from the cardiogram of said living being, said synchronizing means being connected to said waveform memory means for enabling the memory means to accept each waveform signal in succession for storage in said waveform memory means, whereby an integrated measurement of the aggregated blood flow in said limb is provided by the contributions from the switched-in electrodes.

2. Instrument as recited in claim 1, wherein said switching means selectively switch in said pairs of electrodes with one polarity during one cycle of measurements and the reverse polarity during another cycle of measurements.

3. Instrument as recited in claim 1, wherein said switching means includes a counter circuit for counting the pulsatile blood flow waveforms entered into said waveform memory means and control means responsive to a preselected count in said counting means for terminating the storage of waveforms in the memory means for each of said cycles of measurements and for switching-in the next in succession pair of electrodes.

4. Instrument as recited in claim 1, wherein said means for producing a magnetic field includes a pair of permanent magnet means spaced apart to accommodate said limb extending therethrough;
    a metal ring;
    means for mounting said pair of permanent magnet means at diametrically opposite locations on said metal ring, said metal ring being comprised of soft iron constituting a pole piece for closing the path of the magnetic field between said permanent magnet means; and
    means for rotating said permanent magnet means into selected positions around said limb whereby the magnetic field produced by said permanent magnet means can be oriented in directions perpendicular to the line between each switched-in pair of electrodes.

5. Method of measuring the pulsatile blood flow in a limb of a living being, comprising:
    locating a plurality of electrodes in diametrically opposed pairs on the skin of said limb at a plurality of spaced positions around the limb;
    producing a stable and homogeneous magnetic field perpendicular to the limb, the magnetic field having intensity large enough to produce measurable signals in said electrodes in response to pulsatile blood flow through at least one arterial vessel in said limb;

selectively switching-in only one of said pairs of electrodes to the input of a waveform memory means;

orienting said magnetic field in a direction perpendicular to the line between the switched-in pair of electrodes;

counting a predetermined number of waveforms picked up by said switched-in electrodes while the magnetic field is oriented in said perpendicular direction to constitute a first cycle of waveform measurement;

thereafter successively switching-in one at a time the additional pairs of said electrodes for one or more further cycles of measurements;

successively orienting said magnetic field perpendicular to the line between each selected switched-in additional pair of electrodes;

counting the same predetermined number of waveforms to be stored during each further cycle while the magnetic field remains oriented in the perpendicular direction corresponding to each switched-in pair of electrodes; and synchronizing the waveform signals with the cardiogram of the living being for storage in the waveform memory means, whereby a total measurement of the aggregated blood flow in said limb is provided by the contributions from each pair of the switched-in electrodes.

* * * * *

UNITED STATES PATENT AND TRADEMARK OFFICE
CERTIFICATE OF CORRECTION

PATENT NO. : 3,994,285
DATED : November 30, 1976
INVENTOR(S) : Henri Georges Doll It is certified that error appears in the above-identified patent and that said Letters Patent are hereby corrected as shown below:

Column 1, line 25:  "Hq" should be --very--;

Column 1, line 32:  "Hq" should be --periphery--;

Column 9, line 1:  "Hg" should be --Hq--;

Column 9, line 7:  "H8" should be --Hq--;

Column 9, line 11:  "q" should be --Hq--;

Column 9, line 18:  "and" should be --by--.

Cover Page, Item [75]:  "Henry" should be -- Henri --.

Signed and Sealed this

Twenty-second Day of March 1977

[SEAL]

Attest:

RUTH C. MASON
Attesting Officer

C. MARSHALL DANN
Commissioner of Patents and Trademarks